(12) United States Patent
Heatley-Adams et al.

(10) Patent No.: US 8,448,281 B2
(45) Date of Patent: May 28, 2013

(54) DOMESTIC APPLIANCE

(75) Inventors: Emma Jane Heatley-Adams, Malmesbury (GB); Paul Anthony Denney, Malmesbury (GB); Peter David Gammack, Malmesbury (GB); James Dyson, Malmesbury (GB); Jeremy William Crouch, Malmesbury (GB)

(73) Assignee: Dyson Technology Limited, Malmesbury (GB)

( * ) Notice: Subject to any disclaimer, the term of this patent is extended or adjusted under 35 U.S.C. 154(b) by 882 days.

(21) Appl. No.: 12/576,047

(22) Filed: Oct. 8, 2009

(65) Prior Publication Data

US 2011/0083289 A1    Apr. 14, 2011

(51) Int. Cl.
*A46B 13/02* (2006.01)

(52) U.S. Cl.
USPC .......................................................... 15/22.1

(58) Field of Classification Search
USPC ................................................. 15/21.1, 22.1
See application file for complete search history.

(56) References Cited

U.S. PATENT DOCUMENTS

| | | | |
|---|---|---|---|
| 1,671,891 A | | 5/1928 | Dolan |
| 1,927,566 A | * | 9/1933 | Hawk ................................ 15/23 |
| 5,842,244 A | * | 12/1998 | Hilfinger et al. ................ 15/22.1 |
| 5,876,206 A | * | 3/1999 | Maurer .......................... 433/216 |
| 6,032,313 A | | 3/2000 | Tsang |
| 6,338,176 B1 | * | 1/2002 | Smith et al. ........................ 15/28 |
| 2005/0039276 A1 | * | 2/2005 | Kressner et al. ................ 15/22.1 |

FOREIGN PATENT DOCUMENTS

| | | |
|---|---|---|
| DE | 299 08 708 | 10/1999 |
| GB | 2448466 | 10/2008 |
| JP | 4-227209 | 8/1992 |
| WO | WO-2008/125269 | 10/2008 |

OTHER PUBLICATIONS

ISR and Written Opinion mailed Mar. 15, 2011 directed towards International application No. PCT/GB2010/051603; 6 pages.

* cited by examiner

*Primary Examiner* — Laura C Guidotti
(74) *Attorney, Agent, or Firm* — Morrison & Foerster LLP

(57) ABSTRACT

A domestic appliance includes a head divided into a first rotatable member and a second rotatable member, and a drive mechanism for rotating the head about a first axis while simultaneously rotating the first rotatable member about a second axis and the second rotatable member about a third axis. Each of the second axis and the third axis is angled to and preferably intersects the first axis. When viewed in a direction extending along the second axis towards the first axis, the drive mechanism rotates the first rotatable member about the second axis in a first angular direction and the second rotatable member about the third axis in a second angular direction opposite to the first angular direction.

33 Claims, 9 Drawing Sheets

DOMESTIC APPLIANCE

FIELD OF THE INVENTION

The present invention relates to a domestic appliance. The appliance may be used to clean, brush or polish one or more of a wide variety of items, such as human or animal teeth, fingernails, jewellery, glassware, metalware, furniture, shoeware, bathroom fittings and fixtures, pipes, drains, kitchenware, foodstuffs, keyboards, floor surfaces and automobiles.

BACKGROUND OF THE INVENTION

Electric toothbrushes generally impart a brushing action to teeth through oscillatory or rotational motion of one or more parts of a brush head. For example, one known toothbrush comprises a handle and a shaft housing a motor-driven drive mechanism, and a cleaning head having bristles mounted for oscillatory motion by the drive mechanism about an axis transverse to the shaft. Other electric toothbrushes comprise bristles mounted for rotational motion about an axis which is generally parallel to, or co-linear with, the shaft. The bristles may be mounted on a cylindrical brush head for rotation about the longitudinal axis of the head. Alternatively, it is known to mount bristles on a generally spherical brush head which is rotated about the axis of the shaft. For example, WO2008/125269 describes an electric toothbrush in which a spherical brush head is divided into two generally hemispherical sections. The drive mechanism is arranged to rotate the head about a first axis which is co-linear with the longitudinal axis of the shaft, while simultaneously rotating the two hemispherical sections in unison about a second axis orthogonal to the first axis.

SUMMARY OF THE INVENTION

The present invention provides a domestic appliance comprising a head divided into a first rotatable member and a second rotatable member, and a drive mechanism for rotating the head about a first axis while simultaneously rotating the first rotatable member about a second axis and the second rotatable member about a third axis, wherein each of the second axis and the third axis is angled to the first axis, and wherein, when viewed in a direction extending along the second axis towards the first axis, the drive mechanism rotates the first rotatable member about the second axis in a first angular direction and the second rotatable member about the third axis in a second angular direction opposite to the first angular direction.

The contra-rotation of the first rotatable member relative to the second rotatable member, coupled with the rotation of the head about the first axis, has been found to afford a superior cleaning action in comparison to an appliance in which the head is not so divided into first and second rotatable members, and so simply rotates about the first axis. Furthermore, the contra-rotation of the rotatable members means that the rotatable members can impart the same sweeping action over a surface to be treated using the appliance.

The first angular direction in which the first rotatable member rotates about the second axis, when viewed in a direction extending along the second axis towards the first axis, is preferably a clockwise direction when the head is rotated in a clockwise direction as viewed in a direction extending along the first axis towards the head. When the appliance is used as a toothbrush, for example, this can provide a sweeping action in which both of the first and second rotatable members brush along a tooth in a direction extending away from the gum line.

Each of the second axis and the third axis preferably intersects the first axis.

Each of the second axis and the third axis may be substantially orthogonal to the first axis. The second axis and the third axis may be substantially co-linear, or they may be parallel to each other. Alternatively, each of the second axis and the third axis may be inclined relative to the first axis so that the rims of the rotatable members converge. This can enhance the sweeping action of the rotatable members at a particular part of a surface to be treated using the appliance. Therefore, the present invention also provides a domestic appliance comprising a head divided into a first rotatable member and a second rotatable member, and a drive mechanism for rotating the head about a first axis while simultaneously rotating the first rotatable member about a second axis and the second rotatable member about a third axis, wherein each of the second axis and the third axis is inclined relative to the first axis.

The second and third axes may be oriented so that the inclination of the second axis relative to the first axis is the same as the inclination of the third axis relative to the first axis. For example, an angle subtended between the first axis and the second axis, and so between the first axis and the third axis, is preferably an acute angle, which is preferably between 60° and 90°, more preferably between 70° and 85°. However, the inclination of the second axis relative to the first axis may be different from the inclination of the third axis relative to the first axis. This can improve the sweeping action of the rotatable members relative to a particular part of a surface to which the first axis is tangential when the appliance is held by a user.

The first axis may be substantially co-planar with both the second axis and the third axis. Alternatively, the second and third axes may be co-planar and, within that plane, mutually inclined, preferably at an obtuse angle. That plane may be orthogonal to the first axis.

As another alternative, each of the second axis and the third axis may be located within a respective different plane that contains the first axis. Therefore, the present invention also provides a domestic appliance comprising a head divided into a first rotatable member and a second rotatable member, and a drive mechanism for rotating the head about a first axis while simultaneously rotating the first rotatable member about a second axis angled to the first axis and the second rotatable member about a third axis angled to the second axis, wherein each of the second axis and the third axis is located within a respective different plane which contains the first axis. An angle subtended between a first plane, containing the first axis and the second axis, and a second plane, containing the first axis and the third axis, is preferably an obtuse angle which is preferably between 120 and 180°.

Each of the rotatable members is preferably symmetrical about a longitudinal axis thereof, which passes through the centre of its outer surface. Each of the first rotatable member and the second rotatable member may be dome-shaped, and may have a generally spherical curvature. In this case the head may be barrel-shaped, but the head is preferably substantially spherical. As an alternative to dome-shaped rotatable members, each of the first and second rotatable members may comprise a plurality of facets. The number of facets is preferably at least four, and more preferably between four and twelve.

The first rotatable member may be substantially symmetrical about the second axis, and the second rotatable member may be substantially symmetrical about the third axis. Alternatively, the first rotatable member may be asymmetric about the second axis, and the second rotatable member may be asymmetric about the third axis. For example, the rotatable members may be arranged so that at least one of the rotatable members is rotated by the drive mechanism so that the centre of the outer surface of that rotatable member orbits about its axis of rotation. During use, the orbital movement of the centre of each rotatable member about its respective rotational axis can provide an enhanced massaging effect for, for example, cleaning the gums of a user, and for generally improving the cleaning effect of the appliance.

In one embodiment, the rotatable members are arranged so that the first rotatable member is rotated about a second axis which is inclined at an acute angle to its longitudinal axis, and the second rotatable member is rotated about a third axis which is inclined at an acute angle to its longitudinal axis. Each of these acute angles is preferably between 0 and 15°, and the angles may be either similar or dissimilar.

In view of this, the present invention also provides a domestic appliance comprising a head divided into a first rotatable member and a second rotatable member, and a drive mechanism rotating the head about a first axis while simultaneously rotating the first rotatable member about a second axis and the second rotatable member about a third axis, and wherein the first rotatable member is asymmetric about the second axis and the second rotatable member is asymmetric about the third axis.

The drive mechanism may comprise a shaft for rotating the head about the first axis, and an actuator for actuating the rotation of the shaft. The actuator may comprise a motor, which may be readily accommodated within a handle of the appliance, for example. However, alternative types of actuator can include an air-driven actuator, such as a turbine or a pneumatic airline, a water-driven actuator, a steam-driven actuator a mechanically-driven actuator and a hydraulically-driven actuator.

The drive mechanism may comprise a plurality of bevel gears for rotating the rotatable members. Each of these bevel gears may be connected to the shaft for rotation about the first axis, and mesh with a further bevel gear which is not rotated by the shaft so that each of the bevel gears rotates about a respective one of the second axis and the third axis. The first bevel gear preferably has a plurality of teeth which surround the first axis. Alternatively, the plurality of teeth may extend only partially about the first axis. In this case, the rotatable members will only rotate about the second axis and the third axis respectively during part of the rotation of the head about the first axis, for example only when the rotatable member is to engage a surface to be treated. This can prolong the life of the bevel gears.

As an alternative to gears, the drive mechanism may comprise a friction drive for rotating the rotatable members about the second axis and the third axis respectively.

The drive mechanism may comprise a drive shaft which rotates about a fourth axis which is co-linear with the first axis. Alternatively, the drive shaft may rotate about a fourth axis which is angled to the first axis. This can enable the cleaning benefit resulting from the rotation of the head about the first axis, coupled with the simultaneous rotation of each of the first and second rotatable members about a respective one of the second axis and the third axis, to be maximized. For example, an angle subtended between the fourth axis and the first axis may be in the range from 90 to 180°, preferably in the range from 115 to 155°. The head may comprise a head shaft extending therefrom, and which is driven to rotate about the first axis by the drive shaft. Alternatively, the drive shaft may be a curved or flexible drive shaft, which is coupled at one end thereof to an actuator for rotating the drive shaft, and at the other end thereof to the head of the appliance.

Each of the first rotatable member and the second rotatable member may comprise bristles extending outwardly therefrom for brushing an object. Alternatively, each of the rotatable members may comprise a pad, fibres or filaments for cleaning or polishing an object. Where the rotatable members comprise bristles, the bristles may have different lengths. The bristles may extend outwardly from the head at a variety of different angles, and may extend radially or non-radially from the head. The bristles may be arranged in either a regular pattern or a non-regular pattern. The bristles may have a range of different diameters. The bristles may be arranged in a plurality of tufts, with the tufts having a range of different tuft diameters.

Where the second and third axes are mutually inclined, the head may comprise a third member located between the first and second rotatable members and which has tapering side walls. This third member can inhibit the ingress of dirt and debris into the head from between the rims of the rotatable members while, if bristled, contributing to the sweeping action of the head through rotation about the first axis.

The drive mechanism may be arranged to rotate the head periodically in first and second angular directions about the first axis. This will result in the periodic rotation of both the first rotatable member about the second axis and the second rotatable member about the third axis in reverse directions, and so that, at any given time, the first rotatable member is rotating about the second axis in the opposite angular direction to the rotation of the second angular member about the third axis.

A guard may extend partially about the head for inhibiting undesirable contact between the head and, for example, the soft tissue of a user's mouth when the appliance is used as a toothbrush. The guard is preferably shaped to lie adjacent to the outer surface of the head. For example, the guard may be substantially hemispherical, or may comprise a segment of a hemisphere.

The appliance may be in the form of a toothbrush. However, the appliance may be scaled to clean, brush or polish one or more of a wide variety of other objects, such as fingernails, jewellery, glassware, metalware, furniture, shoeware, bathroom fittings and fixtures, pipes, drains, foodstuffs, keyboards, floor surfaces and automobiles

BRIEF DESCRIPTION OF THE DRAWINGS

An embodiment of the present invention will now be described, by way of example only, with reference to the accompanying drawings, in which:

FIG. 1(*b*) is a schematic side cross-sectional view taken along line A-A in FIG. 1(*a*);

FIG. 1(*c*) is a schematic front perspective view of the head of the appliance of FIG. 1(*a*);

FIG. 1(*d*) is a schematic front view of the head of the appliance of FIG. 1(*a*);

FIG. 2(*b*) is a schematic side view of the drive mechanism of FIG. 2(*a*);

FIG. 2(*c*) is a schematic side cross-sectional view taken along line A-A in FIG. 2(*b*);

FIG. 2(*d*) is a schematic front view of the drive mechanism of FIG. 2(*a*);

FIG. 2(*e*) is a schematic top view of the drive mechanism of

DETAILED DESCRIPTION OF THE INVENTION

Figure 1D:
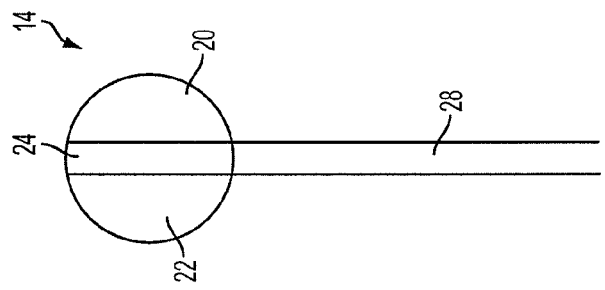
FIG. 1(*a*) is a schematic side view of a first embodiment of a domestic appliance.
Figure 1C:
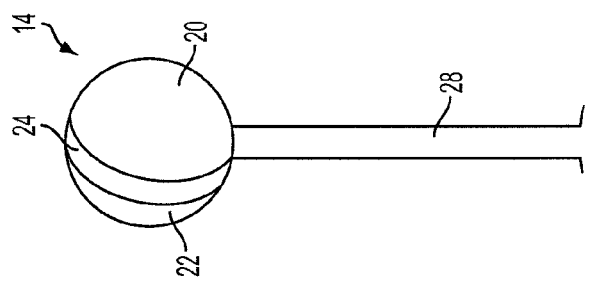

With reference first to FIGS. 1(a) to 1(d), a first embodiment of a domestic appliance 10 comprises a handle 12 and a head 14. The handle 12 houses a motor 16 of a drive mechanism for rotating the head 14 of the appliance 10 relative to the handle 12. The handle 12 may house a battery 18 for supplying power to the motor 16. The battery 18 is preferably a rechargeable battery, such as a nickel-metal hydride battery, and so recharging terminals may be provided on the base of the handle 12 for connection to a recharging base station. Alternatively, the motor 16 may be mains-driven, or driven by a non-rechargeable battery. In this latter case, the battery 18 may be accessed for replacement through separation of two parts of the handle 12.

The head 14 is divided into a first rotatable member 20 and a second rotatable member 22. Each of the rotatable members 20, 22 is symmetrical about a longitudinal axis passing through the centre of its outer surface. In this embodiment, each of the rotatable members 20, 22 is dome-shaped, and has an outer surface with a generally spherical curvature. The head 14 also comprises a substantially annular third member 24 which is located between the rims of the rotatable members 20, 22 to inhibit the ingress of dirt into the head 14 from between the rims of the rotatable members 20, 22. The head 14 is substantially spherical in shape.

Each of the first and second rotatable members 20, 22 and the third member 24 may comprise a plurality of bristles (not shown) extending outwardly therefrom. Alternatively, a cloth or pad comprising fibres, filaments or abrasive medium may be attached to the outer surface of each of the first and second rotatable members 20, 22 and the third member 24.

The drive mechanism comprises a drive shaft 26 which is rotated by the motor 14. The speed at which the drive shaft 26 is rotated by the motor 14 depends on the function of the appliance 10. For example, if the appliance 10 is to be used as a toothbrush then the drive shaft 26 is preferably rotated at a speed in the range from 50 to 2000 revolutions per minute, whereas if the appliance 10 is to be used as a grinding or polishing tool then the drive shaft 26 is preferably rotated at a speed of around several thousand revolutions per minute. However, the speed at which the drive shaft 26 is rotated by the motor 16 is not material to the present invention.

The drive shaft 26 is housed within a sleeve 28 extending between the handle 12 and the head 14, and which remains stationary as the drive shaft 26 is rotated by the motor 16. The drive shaft 26 is arranged to rotate the head 14 about a first axis $A_1$, which in this embodiment is co-linear with the longitudinal axis of the drive shaft 26 and passes through the centre of the head 14. The drive mechanism further comprises a first bevel gear 30 connected to the sleeve 28, a second bevel gear 32 connected to the drive shaft 26 and which meshes with the first bevel gear 30 to rotate about a second axis $A_2$, and a third bevel gear 34 connected to the drive shaft 26 and which meshes with the first bevel gear 30 to rotate about a third axis $A_3$. In this first embodiment, each of the second axis $A_2$ and the third axis $A_3$ is co-planar with, and substantially orthogonal to, the first axis $A_1$. The first rotatable member 20 is connected to the second bevel gear 32 and the second rotatable member 22 is connected to the third bevel gear 34. Consequently, when the motor 16 is actuated, for example in response to a user depressing a switch located on the handle 12, the head 14 is rotated about the first axis $A_1$ while, simultaneously, the first rotatable member 20 is rotated about the second axis $A_2$ and the second rotatable member 22 is rotated about the third axis $A_3$.

Figure 1B:
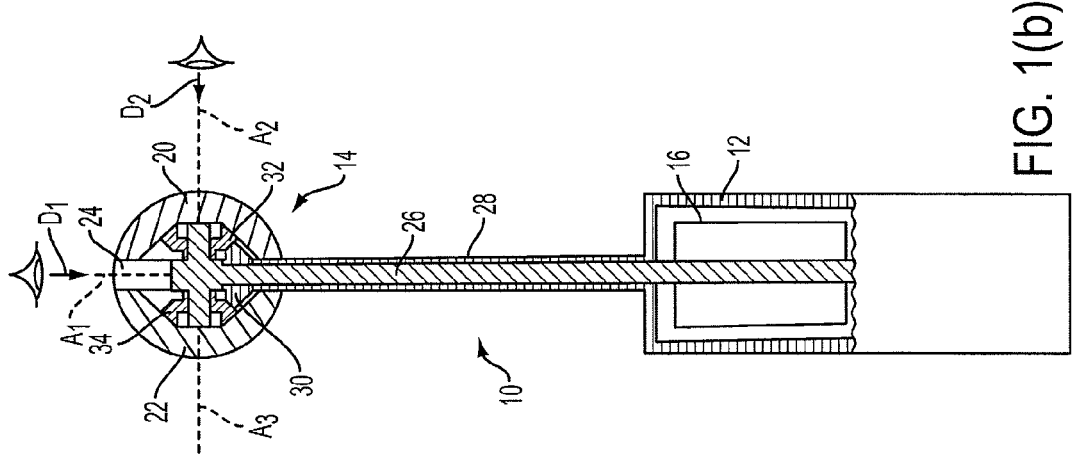
Figure 1A:
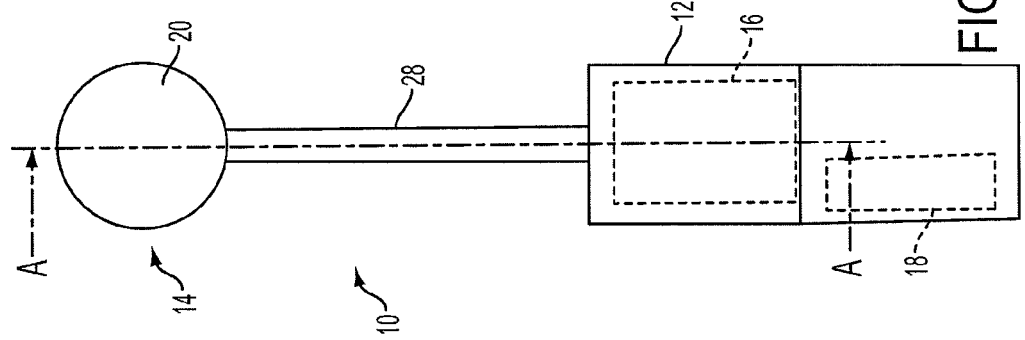

In use, the motor 16 is arranged to rotate the head in a clockwise direction when viewed in a direction $D_1$ (indicated in FIG. 1(b)) extending along the first axis $A_1$ from the head 14 towards the motor 16. When viewed from a direction $D_2$ (also indicated in FIG. 1(b)) which extends along the second axis $A_2$ towards the first axis $A_1$, the first rotatable member 20 rotates in a clockwise direction about the second axis $A_2$ while the second rotatable member 22 rotates in an anti-clockwise direction about the third axis $A_3$. As a result, the first and second rotatable members 20, 22 can impart the same sweeping action over a surface engaged by the head 14 of the appliance 10.

FIGS. 2(a) to 2(e) and FIGS. 3(a) to 3(c) illustrate the head and drive mechanism of a second embodiment of a domestic appliance 40. The handle 12 of the domestic appliance 40 is the same as that of the domestic appliance 10 and so will not be described again here. Similar to the first embodiment, the drive mechanism comprises a drive shaft 42 which is rotated by the motor 16 located within the handle 12, and is housed within a sleeve 44 extending between the handle 12 and the head 46 of the appliance 40. The drive shaft 42 is arranged to rotate the head 46 about a first axis $A_1$, which in this embodiment is also co-linear with the longitudinal axis of the drive shaft 42 and passes through the centre of the head 46. The drive mechanism further comprises a first bevel gear 48 connected to the sleeve 44, a second bevel gear 50 connected to the drive shaft 42 and which meshes with the first bevel gear 48 to rotate about a second axis $A_2$ and a third bevel gear 52 connected to the drive shaft 42 and which meshes with the first bevel gear 48 to rotate about a third axis $A_3$. Thus, the angular directions in which the bevel gears rotate about the axes $A_1$, $A_2$, $A_3$ respectively are the same as the first embodiment.

Figure 2:
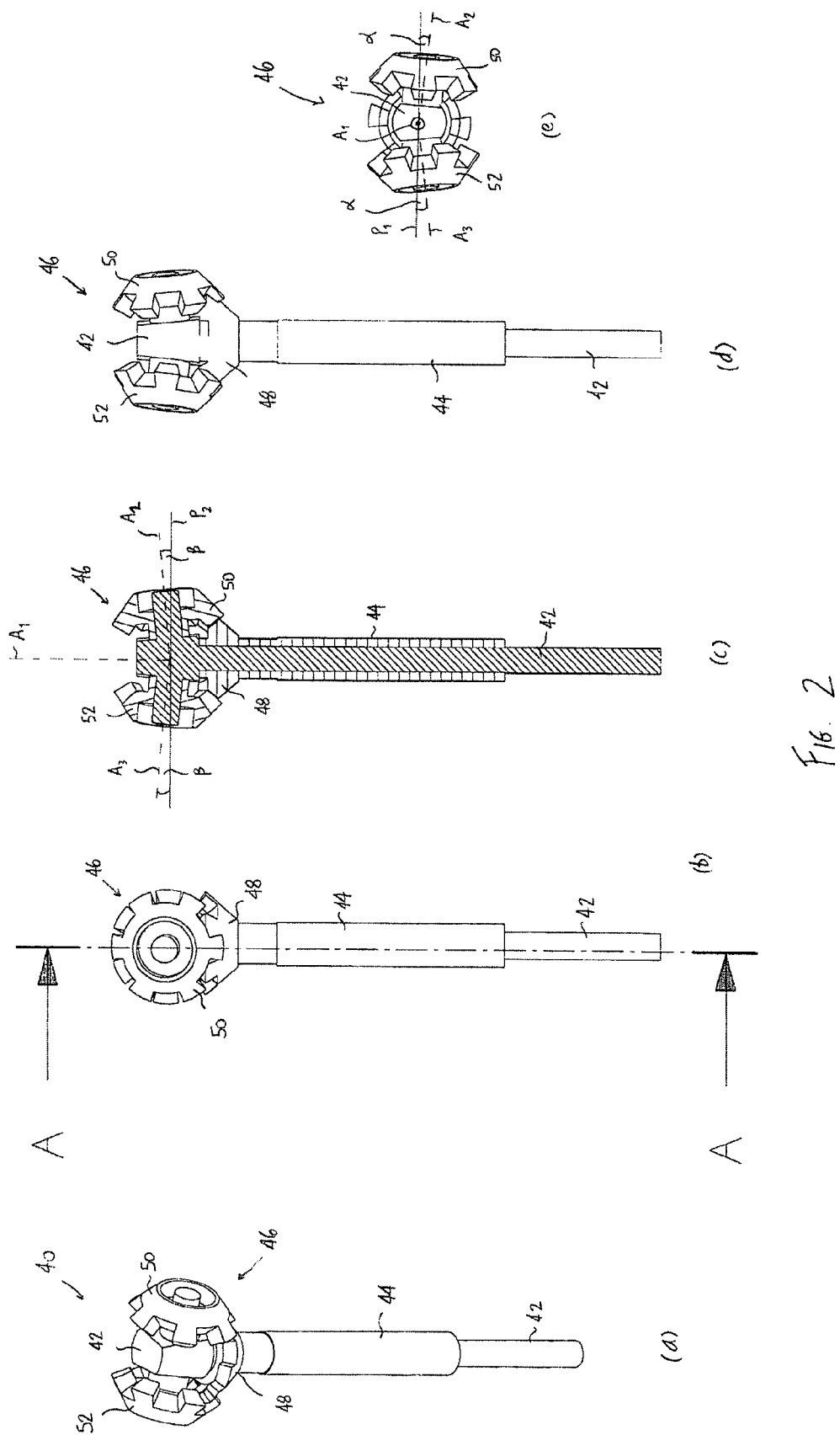
FIG. 2(*a*) is a schematic front perspective view of part of a drive mechanism of a second embodiment of a domestic appliance.

In this second embodiment, however, the second and third axes $A_2$, $A_3$ have a different orientation relative to the first axis $A_1$. As illustrated in FIG. 2(e), in this second embodiment each of the second and third axes $A_2$, $A_3$ is inclined by an angle α relative to a vertical plane $P_1$ containing the first axis $A_1$. In this embodiment the angle α is around 6°. Each of the second and third axes $A_2$, $A_3$ is also inclined by an angle β relative to a horizontal plane $P_2$ orthogonal to the first axis $A_1$ and which passes through the centre of the head 46, as illustrated in FIG. 2(c). In this embodiment the angle β is also around 6°. Thus, the angle subtended between the first axis $A_1$ and the second axis $A_2$, and so between the first axis $A_1$ and the third axis $A_3$, is around 82°. Furthermore, the first and second axes $A_1$, $A_2$ are contained within a first plane, and the first and third axes $A_1$, $A_3$ are contained within a second plane, with these two planes subtending an angle of around 164° therebetween.

Figure 3:
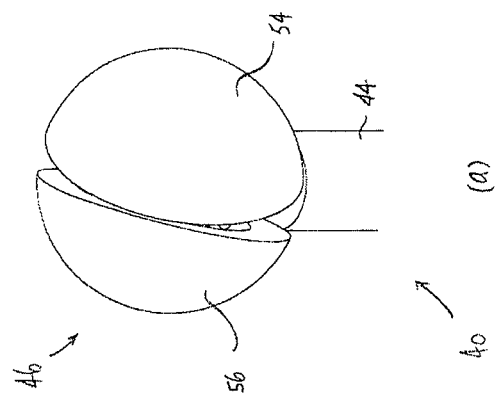
FIG. 3(a) is a schematic front perspective view of part of the second embodiment of a domestic appliance.
FIG. 3(b) is a schematic top view of the appliance of FIG. 3(a)
FIG. 3(c) is a schematic front view of the appliance of FIG. 3(a)
Figure 3:
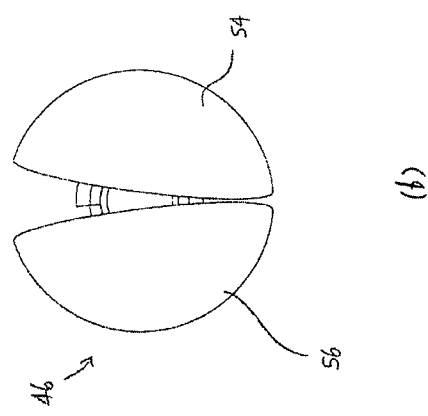
Figure 3:
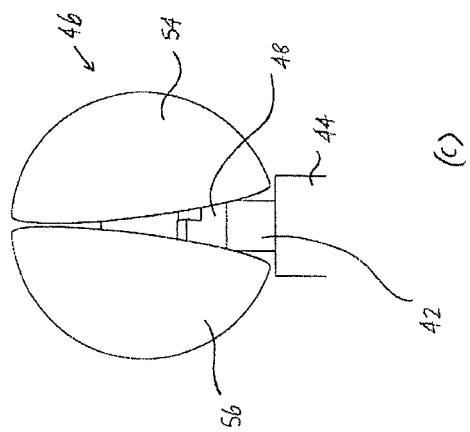

Turning now to FIGS. 3(a) to 3(c), in this second embodiment the head 46 is also divided into a first rotatable member 54 and a second rotatable member 56. As in the first embodiment, each of the rotatable members 54, 56 is dome shaped, and has an outer surface with a generally spherical curvature. The first rotatable member 54 is connected to the second bevel gear 50 and the second rotatable member 56 is connected to the third bevel gear 52. However, due to the inclination of the second and third axes $A_2$, $A_3$ the rims of the rotatable members 54, 56 converge towards a point lying above the plane $P_2$ passing through the centre of the head 46. This can enhance the sweeping action of the rotatable members 54, 56 at a point lying to one side of the first axis $A_1$.

Figure 4:
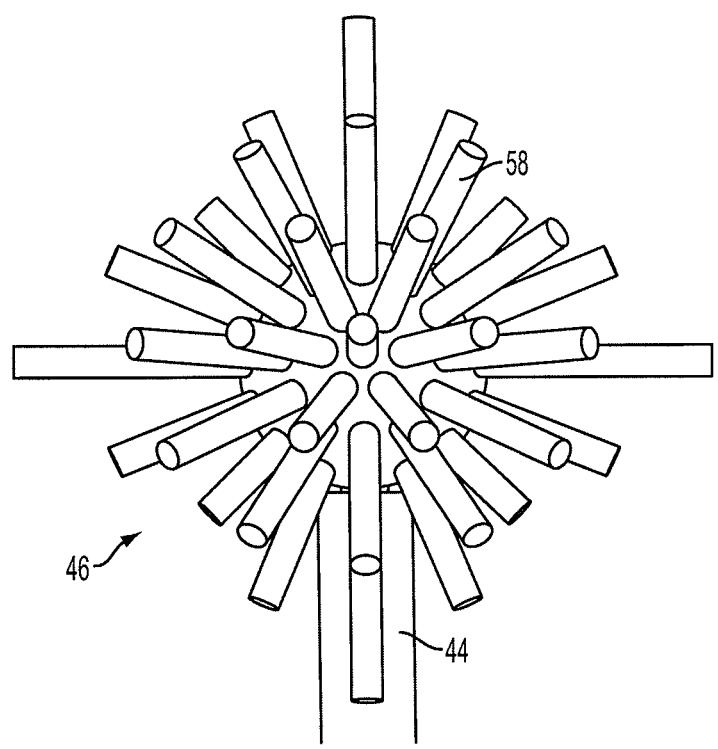
FIG. 4 is a schematic side view of the appliance of FIG. 3(a), but with bristles attached to the rotatable elements of the head.

As illustrated in FIG. 4, each of the first and second rotatable members 54, 56 may comprise a plurality of bristles 58 extending outwardly therefrom. These bristles 58 may have the same length, or they may have a variety of different lengths. In this embodiment, the bristles are arranged in tufts 58 extending outwardly from the head 46. The tufts 58 may have the same external diameter, or a variety of different external diameters. In this embodiment where the appliance 40 is to be used as a toothbrush, the external diameter of the tufts 58 varies between 0.5 and 1.5 mm. The tufts 58 may have different stiffnesses. The stiffness of each tuft 58 may be selected by varying the external diameter of the bristles forming that tuft 58, or by varying the material from which the bristles are formed. In this embodiment, the external diameter of the bristles varies between 0.005 and 0.15 mm. The length of the bristles is in the range from 2 to 10 mm, whereas the external diameter of the head 46 is around 5 mm. Of course, the diameter of the head 46, and the length and the stiffness of the bristles may be varied depending on the intended use of the appliance 40.

Figure 5:
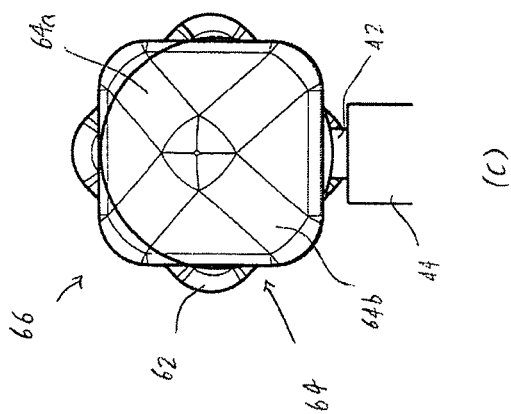
FIG. 5(a) is a schematic front perspective view of the head of a third embodiment of a domestic appliance.
FIG. 5(b) is a schematic top view of the head of FIG. 5(a)
FIG. 5(c) is a schematic side view of the head of FIG. 5(a)
Figure 5:
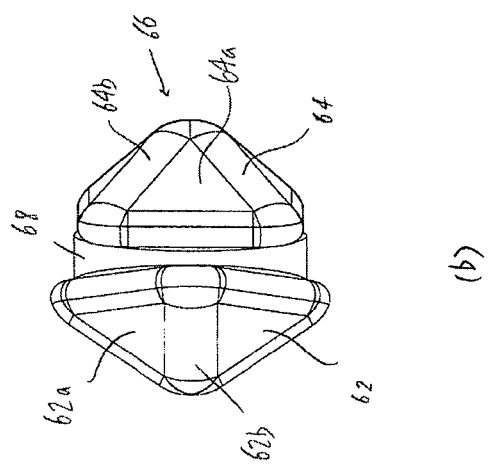
Figure 5:
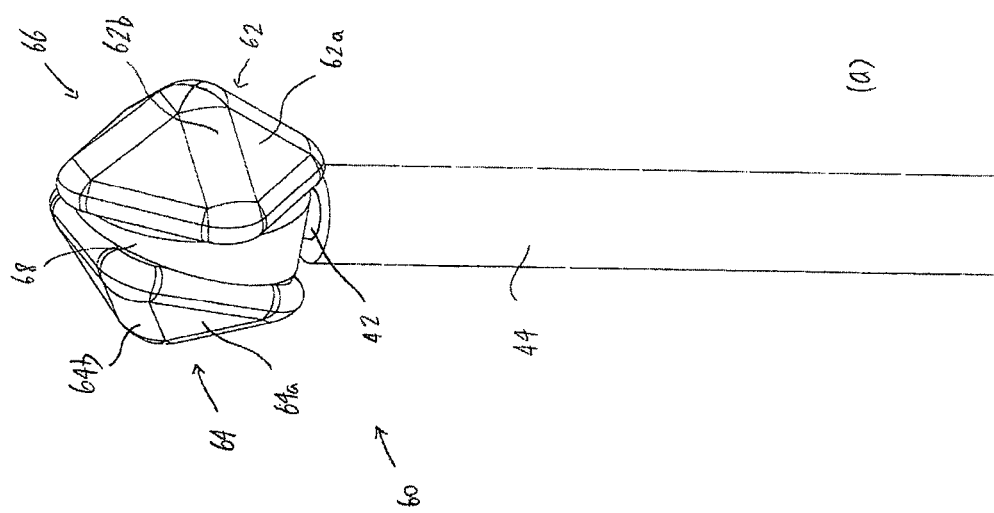

FIGS. 5(a) to 5(c) and 6 illustrate a third embodiment of a domestic appliance 60, which varies from the second embodiment insofar as the shape of the first and second rotatable members 62, 64 connected to the second and third bevel gears 50, 52 of the drive mechanism. In this third embodiment, the outer surfaces of the first and second rotatable members 62, 64 comprise a plurality of facets. Each facet is arranged so as to be inclined towards the longitudinal axis of its rotatable member. In this embodiment each rotatable member 62, 64 comprises eight facets, which include four triangular facets 62a, 64a and four rectangular facets 62b, 64b respectively. However, the total number of facets may be greater or fewer than eight. As illustrated in FIGS. 5(b) and 5(c), the head 66 of the appliance 60 may comprise a third member 68 located between the first and second rotatable members 62, 64 and which has tapering side walls. This third member 68 can inhibit the ingress of dirt and debris into the head 66 from between the rims of the rotatable members 62, 64 while contributing to the sweeping action of the head 66 through rotation about the first axis $A_1$ during use of the appliance 60.

Figure 6:
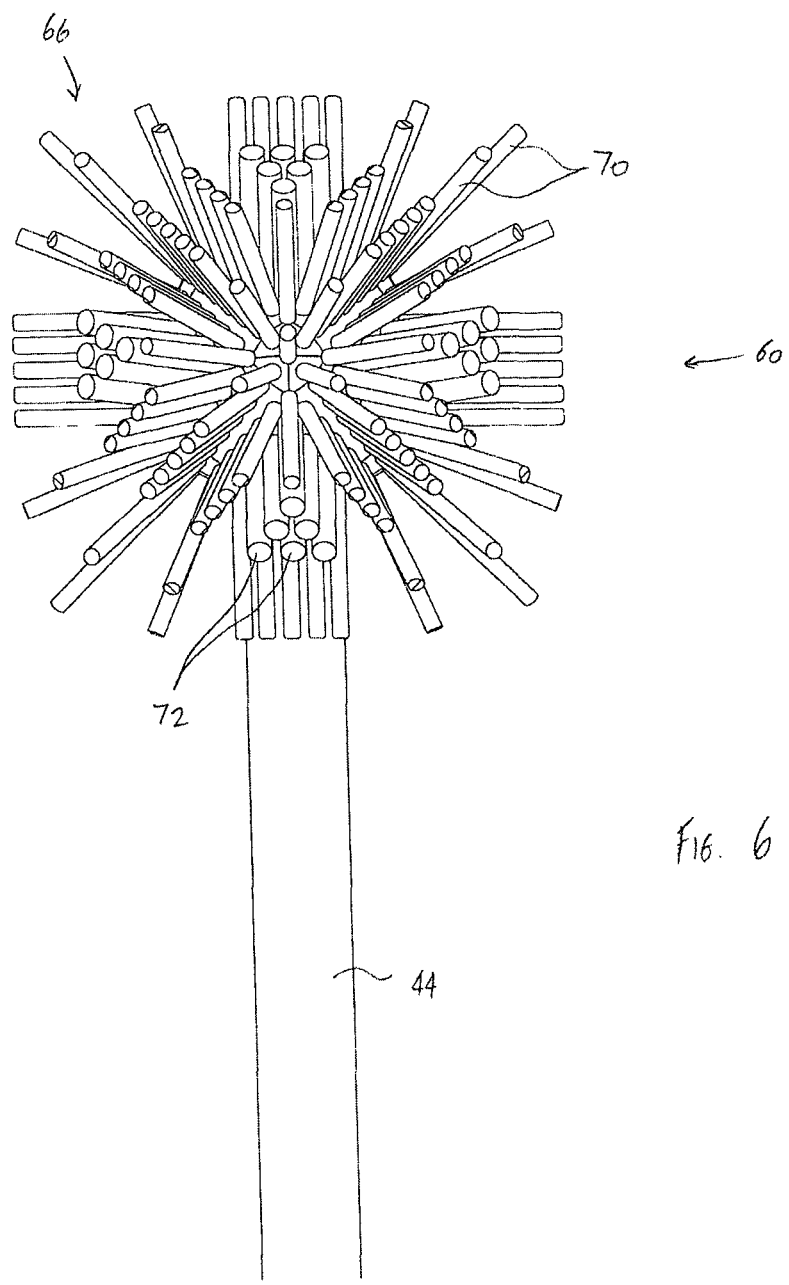
FIG. 6 is a similar view as FIG. 5(c), but with bristles attached to the rotatable elements of the head.
Figure 7:
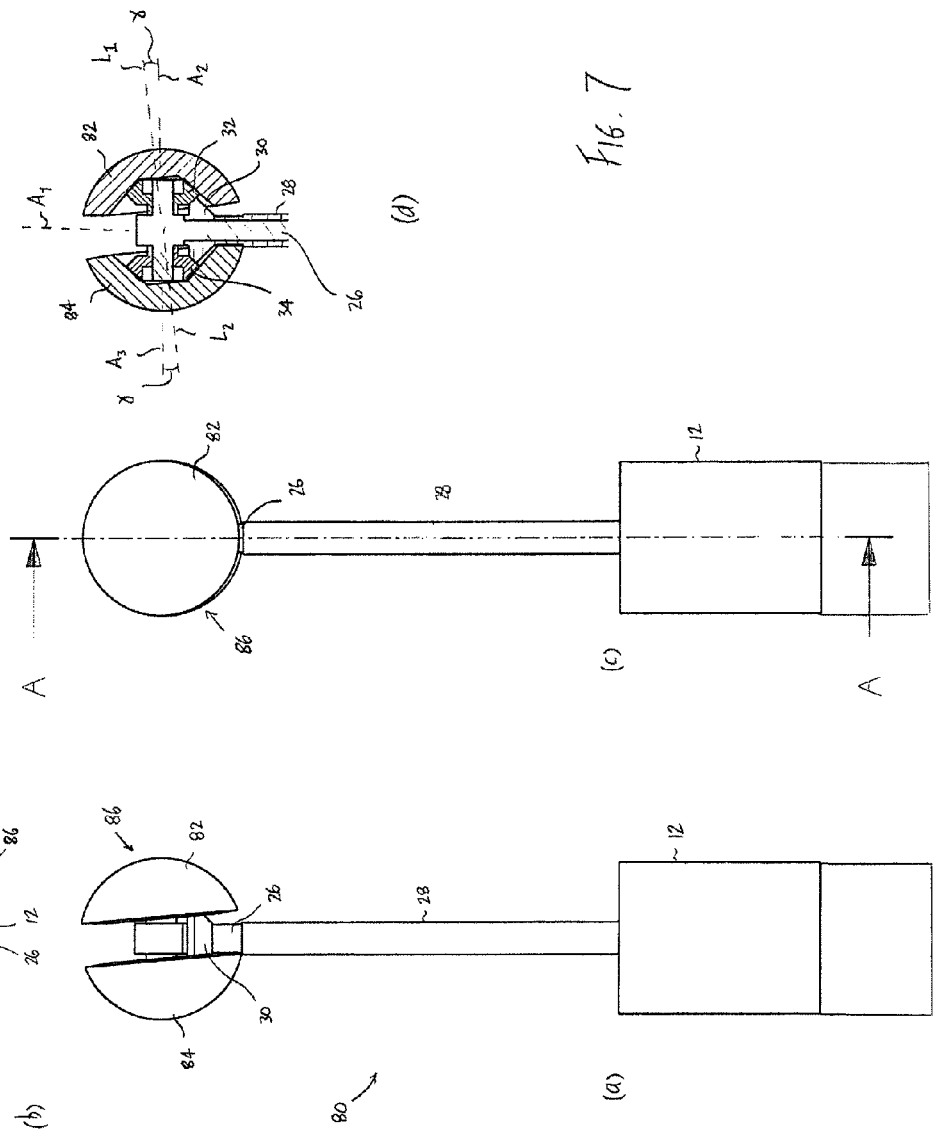
FIG. 7(a) is a schematic front view of a fourth embodiment of a domestic appliance.
FIG. 7(b) is a schematic top view of the appliance of FIG. 7(a)
FIG. 7(c) is a schematic side view of the appliance of FIG. 7(a)
FIG. 7(d) is a schematic side cross-sectional view taken along line A-A in FIG. 7(c)

As illustrated in FIG. 6, bristles may be connected to and extend outwardly from each facet of each rotatable member 62, 64. In this embodiment, the tufts 70 of bristles connected to the rectangular facets 62b, 64b of the rotatable members 62, 64 are formed from relatively long, relatively flexible bristles, whereas the tufts 72 of bristles connected to the triangular facets 62a, 64a of the rotatable members 62, 64 are formed from relatively short, relatively stiff bristles. Where the appliance 60 is to be used as a toothbrush, the tufts 72 of bristles can enhance polishing and removal stains from the teeth of the user, whereas the tufts 70 of the bristles can enhance deep cleaning between the teeth of the user.

FIGS. 7(a) to 7(d) illustrate a fourth embodiment of a domestic appliance 80, which varies from the first embodiment insofar as the first rotatable member 82 is asymmetric about the second axis $A_2$, and the second rotatable member 84 is asymmetric about the third axis $A_3$. In this embodiment, each of the rotatable members 82, 84 is symmetrical about a longitudinal axis passing through the centre of its outer surface. The first rotatable member 82 is connected to the second bevel gear 32 so that the longitudinal axis $L_1$ of the first rotatable member 82, which passes through the centre of the outer surface of the first rotatable member 82, is inclined at an acute angle γ to the second axis $A_2$, and the second rotatable member 84 is connected to the third bevel gear 34 so that the longitudinal axis $L_2$ of the second rotatable member 84, which passes through the centre of the outer surface of the second rotatable member 84, is inclined at an acute angle γ to the third axis $A_3$. In this embodiment, the acute angle γ is around 5°. The first and second rotatable members 82, 84 are therefore asymmetrically arranged about the first axis $A_1$. Consequently, the centre of the outer surface of the first rotatable member 82 orbits about the second axis $A_2$, and the centre of the outer surface of the second rotatable member 84 orbits about the third axis $A_3$ as the head 86 of the appliance 80 is rotated about the first axis $A_1$. This can enhance a massaging effect applied to, for example, the gums of the user. In this embodiment, the longitudinal axes $L_1$, $L_2$ are substantially co-linear, but they may be mutually inclined. The rotatable members 82, 84 are preferably dome-shaped, and have circular rims which are substantially parallel when the rotatable members 82, 84 are connected to the drive mechanism.

Figure 8A:
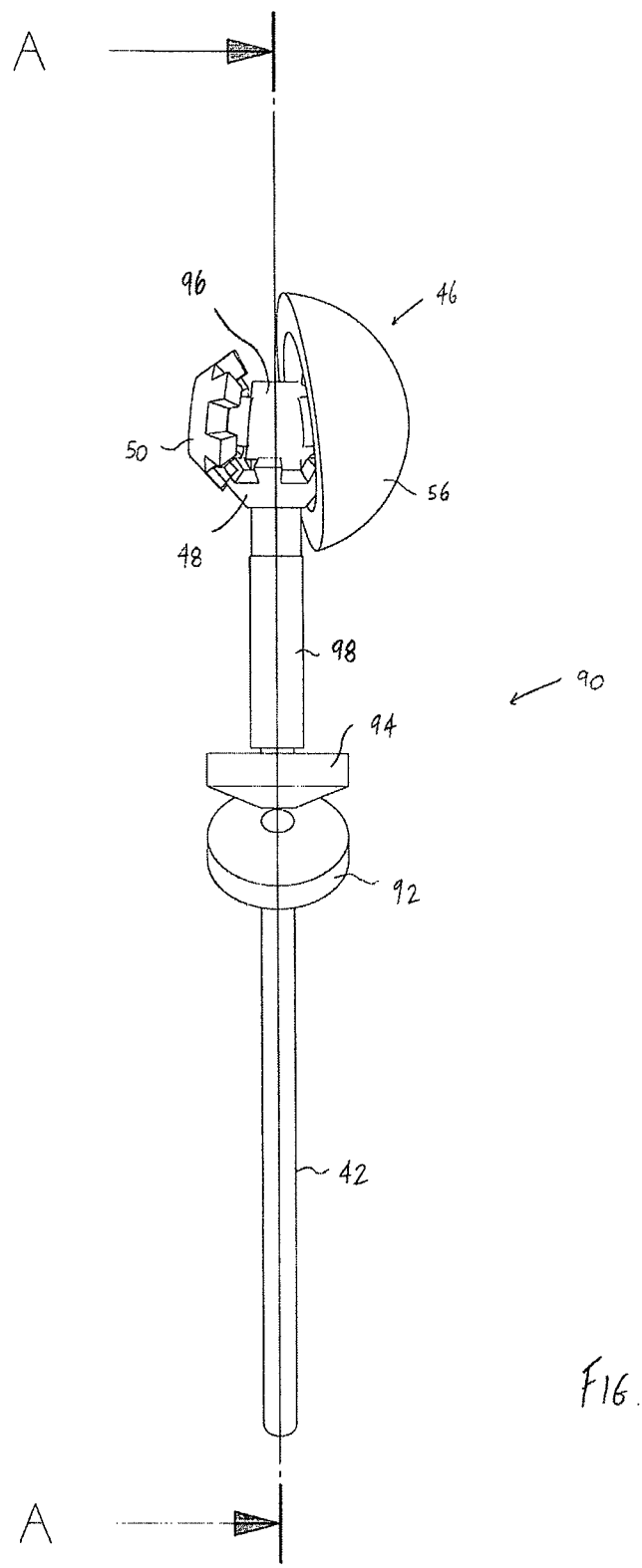
FIG. 8(a) is a schematic rear view of a drive mechanism of a fifth embodiment of a domestic appliance.
Figure 8B:
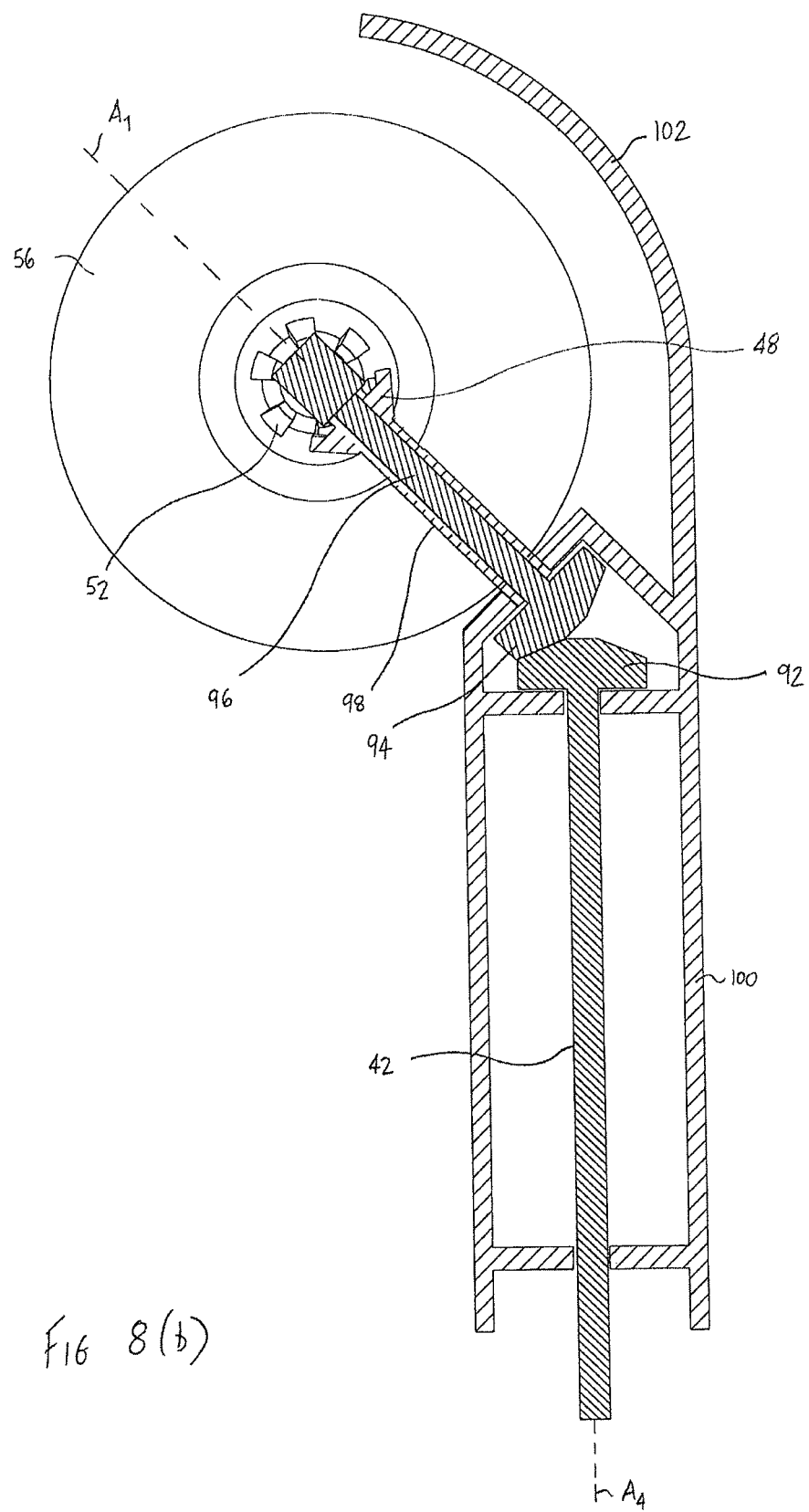
FIG. 8(b) is a schematic side cross-sectional view taken along line A-A of FIG. 8(a), and with part of the drive mechanism located within a housing.

In each of the first to fourth embodiment, the head of the appliance is connected to one end of the drive shaft 26, 42 coupled to the motor 16. A drive mechanism for a fifth embodiment of a domestic appliance 90 is illustrated in FIGS. 8(a) and 8(b). The drive mechanism varies from that of the domestic appliance 40 in that a fourth bevel gear 92 is connected to the end of the drive shaft 42 which is remote from the motor 16. The fourth bevel gear 92 meshes with a fifth bevel gear 94 connected to one end of a head shaft 96. The second and third bevel gears 50, 52 are connected to the other end of the head shaft 96 in a similar manner to their connection to the drive shaft 42 of the appliance 40. The fourth and fifth bevel gears 92, 94 are arranged so that the head shaft 96 is inclined at an obtuse angle to the drive shaft 42. Consequently, the drive shaft 42 rotates about a fourth axis $A_4$ which is angled to the first axis $A_1$. In this example, the angle subtended between fourth axis $A_4$ and the first axis $A_1$ is around 135°. This inclination of the first axis $A_1$ can enable the head of the appliance 90 to contact a surface at such an angle which maximises the benefit of the rotation of the head about the first axis with the simultaneous rotation of each of the rotatable members about a respective one of the second axis and the third axis.

The first bevel gear 48, which meshes with the second and third bevel gears 50, 52, is connected to one end of a sleeve 98 extending about the head shaft 96 so that the head shaft 96 is rotatable relative to the sleeve 98. The other end of the sleeve 98 is connected to a housing 100 coupled to the handle 12 of the appliance 90. The drive shaft 42 and the fourth and fifth bevel gears 92, 94 are located within the housing 100, which serves to inhibit the ingress of dirt or other detritus between the teeth of these bevel gears 92, 94. As illustrated in FIG. 8(b), the housing 100 may comprise a curved guard 102 which extends partially about the external periphery of the head of the appliance 90. The guard 102 may serve to inhibit contact between the head and, for example the soft tissue of the mouth of a user when the appliance 90 is used as a toothbrush.

The invention is not limited to the detailed description given above. Variations will be apparent to the person skilled in the art.

For example, the scale of the appliance may be varied so that the appliance is more suitable for brushing, cleaning or polishing one or more of a wide variety of different objects, including, but not limited to, fingernails, jewellery, glassware, metalware, furniture, shoeware, bathroom fittings and fixtures, pipes, drains foodstuffs, keyboards, floor surfaces and automobiles. The appliance may also be used for non-domestic purposes. Depending on the nature of the surface to be contacted by the bristles of the head, at least one of the stiffness, length and composition of the bristles may be varied as appropriate. Alternatively, a sheet of abrasive material, such as sandpaper, may be connected to the outer surfaces of each of the members of the head so that the appliance may be used as an abrading or grinding tool.

The invention claimed is:

1. A domestic appliance comprising:
    a head divided into a first rotatable member and a second rotatable member; and
    a drive mechanism for rotating the head about a first axis while simultaneously rotating the first rotatable member about a second axis and the second rotatable member about a third axis;
    wherein each of the second axis and the third axis is angled to the first axis, wherein, when viewed in a direction extending along the second axis towards the first axis, the drive mechanism rotates the first rotatable member about the second axis in a first angular direction and the second rotatable member about the third axis in a second angular direction opposite to the first angular direction, and wherein each of the second axis and the third axis is inclined at an acute angle to the first axis.

2. The appliance of claim 1, wherein the inclination of the second axis to the first axis is the same as the inclination of the third axis to the first axis.

3. The appliance of claim 2, wherein an angle subtended between the first axis and the second axis is between 60° and 90°.

4. The appliance of claim 1, wherein the first axis is substantially co-planar with the second axis.

5. The appliance of claim 1, wherein the first axis and the second axis are located in a first plane, and the first axis and the third axis are located in a second plane which is different from the first plane.

6. The appliance of claim 5, wherein an angle subtended between the first plane and the second plane is between 90 and 180°.

7. The appliance of claim 1, wherein the drive mechanism comprises a drive shaft which rotates about a fourth axis, and wherein the first axis is angled to the fourth axis.

8. The appliance of claim 7, wherein an angle subtended between the first axis and the fourth axis is between 90 and 180°.

9. The appliance of claim 1, wherein each of the first rotatable member and the second rotatable member is dome-shaped.

10. The appliance of claim 9, wherein each of the first rotatable member and the second rotatable member has a generally spherical curvature.

11. The appliance of claim 1, wherein each of the first rotatable member and the second rotatable member comprises a plurality of facets.

12. The appliance of claim 1, wherein each of the first rotatable member and the second rotatable member comprises bristles extending outwardly therefrom.

13. The appliance of claim 12, wherein the bristles have different lengths.

14. The appliance of claim 1, comprising a guard extending partially about the head.

15. The appliance of claim 1, wherein the drive mechanism comprises a plurality of bevel gears.

16. The appliance of claim 1, in the form of a toothbrush.

17. A domestic appliance comprising:
    a head divided into a first rotatable member and a second rotatable member; and
    a drive mechanism for rotating the head about a first axis while simultaneously rotating the first rotatable member about a second axis and the second rotatable member about a third axis;
    wherein each of the second axis and the third axis is angled to the first axis, wherein, when viewed in a direction extending along the second axis towards the first axis, the drive mechanism rotates the first rotatable member about the second axis in a first angular direction and the second rotatable member about the third axis in a second angular direction opposite to the first angular direction, and wherein each of the first rotatable member and the second rotatable member is dome-shaped.

18. The appliance of claim 17, wherein each of the second axis and the third axis is substantially orthogonal to the first axis.

19. The appliance of claim 17, wherein the drive mechanism comprises a drive shaft which rotates about a fourth axis, and wherein the first axis is angled to the fourth axis.

20. The appliance of claim 19, wherein an angle subtended between the first axis and the fourth axis is between 90 and 180°.

21. The appliance of claim 17, wherein each of the first rotatable member and the second rotatable member has a generally spherical curvature.

22. The appliance of claim 21, wherein the head is spherical.

23. The appliance of claim 17, wherein each of the first rotatable member and the second rotatable member comprises bristles extending outwardly therefrom.

24. The appliance of claim 23, wherein the bristles have different lengths.

25. The appliance of claim 17, comprising a guard extending partially about the head.

26. The appliance of claim 17, in the form of a toothbrush.

27. A domestic appliance comprising:
    a head divided into a first rotatable member and a second rotatable member; and
    a drive mechanism for rotating the head about a first axis while simultaneously rotating the first rotatable member about a second axis and the second rotatable member about a third axis;
    wherein each of the second axis and the third axis is angled to the first axis, wherein, when viewed in a direction extending along the second axis towards the first axis, the drive mechanism rotates the first rotatable member about the second axis in a first angular direction and the second rotatable member about the third axis in a second angular direction opposite to the first angular direction, and wherein the first rotatable member has a longitudinal axis which is inclined at an acute angle to the second axis, and the second rotatable member has a longitudinal axis which is inclined at said acute angle to the third axis.

28. The appliance of claim 27, wherein the drive mechanism comprises a drive shaft which rotates about a fourth axis, and wherein the first axis is angled to the fourth axis.

29. The appliance of claim 28, wherein an angle subtended between the first axis and the fourth axis is between 90 and 180°.

30. The appliance of claim 27, comprising a guard extending partially about the head.

31. The appliance of claim 27, wherein the first rotatable member is asymmetric about the second axis and the second rotatable member is asymmetric about the third axis.

32. The appliance of claim 27, wherein the acute angle is between 0 and 15°.

33. The appliance of claim 27, in the form of a toothbrush.

* * * * *